(12) United States Patent
Van Landuyt

(10) Patent No.: US 6,698,430 B2
(45) Date of Patent: Mar. 2, 2004

(54) LARYNGEAL MASK ASSEMBLIES

(75) Inventor: Christophe Van Landuyt, London (GB)

(73) Assignee: Smiths Group PLC, London (GB)

( * ) Notice: Subject to any disclaimer, the term of this patent is extended or adjusted under 35 U.S.C. 154(b) by 0 days.

(21) Appl. No.: 10/041,738

(22) Filed: Jan. 10, 2002

(65) Prior Publication Data

US 2002/0112727 A1 Aug. 22, 2002

(30) Foreign Application Priority Data

Feb. 16, 2001 (GB) .............................. 0103813

(51) Int. Cl.[7] .............................. A61M 16/00
(52) U.S. Cl. ............................ 128/207.15; 128/207.14; 128/200.26
(58) Field of Search ............... 128/207.14, 207.15, 128/200.26; 604/96.01

(56) References Cited

U.S. PATENT DOCUMENTS

| | | | | |
|---|---|---|---|---|
| 5,339,805 A | * | 8/1994 | Parker | 128/200.26 |
| 5,850,832 A | * | 12/1998 | Chu | 128/200.26 |
| 6,003,510 A | * | 12/1999 | Anunta | 128/200.26 |
| 6,053,166 A | * | 4/2000 | Gomez | 128/200.26 |
| 6,079,409 A | * | 6/2000 | Brain | 128/200.26 |
| 6,095,144 A | * | 8/2000 | Pagan | 128/207.15 |
| 6,119,695 A | * | 9/2000 | Augustine et al. | 128/207.15 |
| 6,142,144 A | * | 11/2000 | Pacey | 128/200.26 |
| 6,374,827 B1 | * | 4/2002 | Bowden et al. | 128/207.14 |
| 6,378,521 B1 | * | 4/2002 | Van Den Berg | 128/207.14 |
| 6,386,199 B1 | * | 5/2002 | Alfery | 128/207.15 |
| 6,439,232 B1 | * | 8/2002 | Brain | 128/207.15 |

FOREIGN PATENT DOCUMENTS

| | | | | |
|---|---|---|---|---|
| GB | 2317342 | | 3/1998 | |
| GB | 2324737 | | 11/1998 | |
| GB | 2324737 A | * | 11/1998 | .......... A61M/16/04 |

* cited by examiner

Primary Examiner—Aaron J. Lewis
Assistant Examiner—Mital Patel
(74) Attorney, Agent, or Firm—Louis Woo

(57) ABSTRACT

A laryngeal mask has a blocker at its patient end to prevent entry of the epiglottis during insertion. The blocker has a tear-drop shape plate retained around its edge in grooves in the mask and attached to a flexible strip extending along the outside of the assembly.

11 Claims, 1 Drawing Sheet

LARYNGEAL MASK ASSEMBLIES

BACKGROUND OF THE INVENTION

This invention relates to laryngeal mask assemblies.

It is common practice to use an airway known as a laryngeal mask for administering anaesthetic and ventilation gases to a patient. These airways comprise a tube with an inflatable mask or cuff at one end, the tube being inserted in the patient's mouth so that one end is located in the hypopharynx and so that the mask forms a seal in this region with the surrounding tissue. Laryngeal masks are described in, for example, U.S. Pat. Nos. 5,355,879, 5,305,743, 5,297,547, 5,282,464, GB 2267034, U.S. Pat. Nos. 5,249,571, 5,241,956, 5,303,697, GB 2249959, GB 2111394, EP 448878, U.S. Pat. No. 4,995,388, GB 2205499, GB 2128561, GB 2298797 and GB 2334215.

Laryngeal masks have several advantages over endotracheal tubes, which are longer and seal with the trachea below the vocal folds. One potential problem with laryngeal masks is that there is a risk that they may be blocked by the epiglottis during insertion.

BRIEF SUMMARY OF THE INVENTION

It is an object of the present invention to provide an alternative laryngeal mask assembly.

According to the present invention there is provided a laryngeal mask assembly comprising a tube and a mask at the patient end of the tube, the mask including a sealing cuff adapted to seal in the region of the hypopharynx, the cuff extending in a substantially oval configuration and being inclined relative to the axis of the tube, and the cuff enclosing a central region of generally oval shape, the assembly including a blocker member having a plate member at the patient end of an elongate member, the plate member extending generally laterally across the mask to restrict entry of the epiglottis during insertion, and the elongate member extending longitudinally along the assembly such that the blocker member can be removed by pulling rearwardly on the elongate member.

The elongate member may be a strip and it may be flexible. The elongate member preferably extends externally along the assembly. An edge of the plate member preferably engages a surface formation, such as a groove, on the mask. The plate member may be of tear-drop shape.

A laryngeal mask airway assembly according to the present invention will now be described, by way of example, with reference to the accompanying drawings.

DETAILED DESCRIPTION OF THE DRAWINGS

Figure 1:
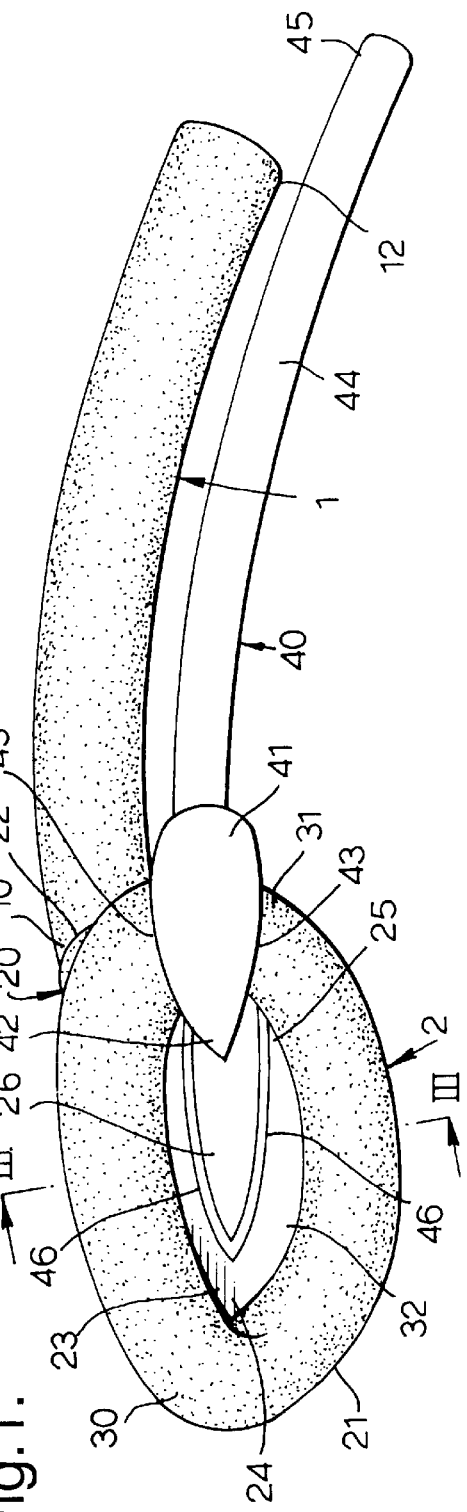
FIG. 1 is a perspective view of the assembly.
Figure 3:
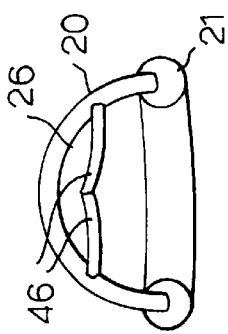
FIG. 3 is a lateral sectional view along the line III—III of FIG. 1.

The laryngeal mask assembly comprises a tube 1 with a mask 2 mounted at the patient end 10 of the tube and a removable blocker 40.

The tube 1 is of a bendable plastics material, such as PVC and is curved along its length from its patient end 10 to its machine end 12. The mask 2 comprises a mount 20 and an inflatable cuff 21. The mount 20 is of a relatively stiff plastics material and is of generally shoe shape. The rear, machine end of the mount has a neck 22 of circular section embracing and bonded to the patient end 10 of the tube 1. The mount 20 tapers outwardly from the machine end 22 to its patient end 23, which is inclined to the axis of the machine end at an angle of about 25° so that the patient end of the mount has an oval shape with its forward end 24 being more pointed than its rear end 25. The patient end 23 of the mount 20 is inclined to face towards the inner side of the curve of the tube 1. Internally, the machine end 22 of the mount 20 communicates with a cavity 26 in the mount that increases in cross-sectional area along its length, from the machine end.

The cuff 21 is tubular and of a thin flexible plastics material. The cuff 21 is formed into an annulus of the same shape as the patient end 23 of the mount 20 so that it is oval with its forwardly-directed end 30 being more pointed than its rearwardly-directed end 31. The cuff 21 encloses a central region 32 of the same shape as the patient end 23 of the mount 20. The cuff 21 is attached around the patient end 23 of the mount 20 such as by means of an adhesive. The cuff 21 is inflated and deflated by means of an inflation line (not shown), which may be a separate small-bore tube communicating with the interior of the cuff and extending rearwardly along the outside of the tube. Alternatively, the inflation line may include a small-bore, minor lumen extending within the wall of the main tube. When inflated in position in a patient, the cuff 21 expands to contact patient tissue in the region of the hypopharnyx with its forward end 30 located against and blocking the opening of the oesophagus.

The blocker 40 is used during insertion of the laryngeal mask airway and is then removed. The blocker 40 comprises a thin, bendable plate or planar member 41 of a plastics material having a tear-drop shape with a pointed forward end 42 and two curved edges 43. The rear end of the plate 41 is attached with an elongate member in the form of a strip 44 of a flexible plastics material. The strip 44 extends externally longitudinally of the assembly and is slightly longer than the laryngeal mask so that its rear or machine end 45 protrudes from the mouth of the patient during use. The blocker 40 is attached with the laryngeal mask during insertion by engagement of the plate 41 with the inside of the mount 20. More particularly, the edges 43 of the plate 41 locate in two grooves 46 formed on the inside surface of the mount 20. The plate 41 is slightly wider than the separation between the grooves 46 so that, when the plate is fitted, it is squeezed laterally and bowed slightly forwardly, producing a secure friction fit.

Figure 2:
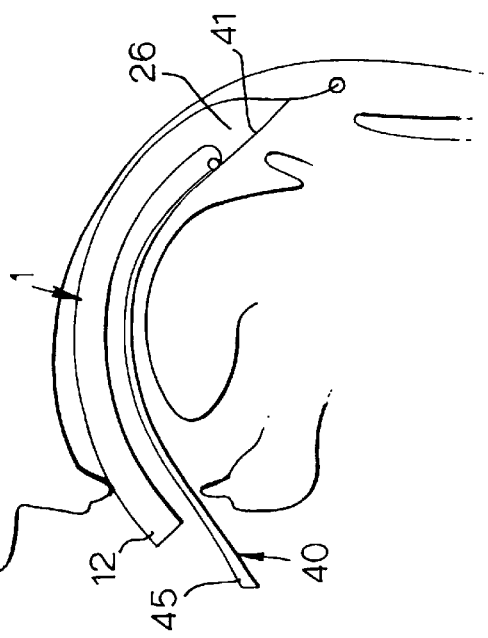
FIG. 2 is a cross-sectional, side elevation view showing the assembly in use in a patient.

The laryngeal mask assembly is inserted in the patient with the blocker 40 attached to the laryngeal mask, as shown in FIG. 2, so that the plate 41 prevents the epiglottis entering the cavity 26 of the mount 20. The strip 44 of the blocker 40 may be pulled rearwardly slightly during insertion so as to flex the mask 2 forwardly slightly and thereby push the epiglottis and the base of the tongue forward. This helps fold up the epiglottis and ensure that it is always located under the proximal side of the sealing cuff 21. When the airway is correctly located, the user simply pulls on the machine end 45 of the blocker strip 44 so as to pull the plate 41 out of the grooves 46 and to pull out the blocker 40 by sliding between the outside of the airway and the pharynx. The shape and nature of the blocker 40 ensure that it can be pulled out along the outside of the larnygeal mask atraumatically.

The blocker could be modified in various ways. The plate could be preformed with a profiled shape, such as a convex shape, on its outwardly-facing surface to improve insertion and to reduce trauma on removal. The elongate member could be rigid so as to give extra rigidity to the assembly, which may facilitate insertion. The plate could have venting holes formed through it to enable the patient to breath during insertion or gaps could be provided between the plate and the mount for this purpose. The plate could be fitted with the mask by some means other than the groove and edge engagement, such as, for example, by some form of clip or tearable bond.

The arrangement of the present invention has various advantages. It ensures that the epiglottis does not block the airway during its insertion. It requires little modification to the laryngeal mask and can be provided at low cost so that it can be disposed of after a single use. Its use is optional since the laryngeal mask can be inserted without the blocker if the user prefers. Once the laryngeal mask has been installed and the blocker removed, it presents no obstacle to air flow along the laryngeal mask or to visualization and insertion of instruments through the laryngeal mask. The blocker can facilitate insertion of the laryngeal mask airway by reducing the need for airway alignment and cricoid traction so that it is possible for the airway to be inserted by one person. It also enables the airway to be inserted more deeply so that the seal on the oesophagus is improved.

What is claimed is:

1. A laryngeal mask assembly comprising: a tube; a mask at a patient end of said tube; a sealing cuff adapted to seal in the region of the hypopharynx, said cuff extending in a substantially oval configuration and being inclined relative to the axis of said tube, and said cuff enclosing a central region of generally oval shape; and a removable blocker member, said blocker member including an elongate member and a plate member at a patient end of said elongate member, wherein said plate member extends generally laterally across said mask to restrict entry of the epiglottis during insertion, and wherein said elongate member extends longitudinally along said assembly such that said blocker member can be removed from said assembly by pulling rearwardly on said elongate member.

2. A laryngeal mask assembly according to claim 1, wherein said elongate member is a strip.

3. A laryngeal mask assembly according to claim 1, wherein said elongate member is flexible.

4. A laryngeal mask assembly according to claim 1, wherein said elongate member extends externally along said assembly.

5. A laryngeal mask assembly according to claim 1; wherein an edge of said plate member engages a surface formation on said mask.

6. A laryngeal mask assembly according to claim 5, wherein said surface formation on said mask is a groove.

7. A laryngeal mask assembly according to claim 1, wherein said plate member is of tear-drop shape.

8. A laryngeal mask assembly comprising: a tube; a mask at a patient end of said tube; a sealing cuff adapted to seal in the region of the hypopharynx, said cuff extending in a substantially oval configuration and being inclined relative to the axis of said tube, and said cuff enclosing a central region of generally oval shape; and removable blocker means for restricting entry of the epiglottis to the mask during insertion, said blocker means including an elongate member extending longitudinally externally of the assembly and a plate member at a patient end of said elongate member and removably secured with said mask such that said blocker means can be removed from said assembly by pulling rearwardly on said elongate member.

9. A laryngeal mask assembly comprising: a tube; a mask at a patient end of said tube; a sealing cuff adapted to seal in the region of the hypopharynx, said cuff extending in a substantially oval configuration and being inclined relative to the axis of said tube, and said cuff enclosing a central region of generally oval shape; and a blocker member, said blocker member including an elongate strip and a plate member at a patient end of said elongate member, wherein said plate member and mask have engaging surface formations so that said plate member is removably located with said mask and extends generally laterally across said mask to restrict entry of the epiglottis during insertion, and wherein said elongate strip extends longitudinally externally along said assembly such that said blocker member can be removed externally between said assembly and the patient by pulling rearwardly on said strip.

10. A method of inserting a laryngeal mask assembly comprising the steps of providing a laryngeal mask assembly having a removable blocker member a part of which extends generally laterally across the mask to restrict entry of the epiglottis; inserting the assembly with the blocker in position into the patient; and subsequently removing the blocker externally between outside of the assembly and the patient.

11. A method according to claim 10, wherein the blocker includes an elongate member extending externally of the assembly, and wherein the method includes the step of gripping the elongate member towards its machine end and pulling it so that the blocker is removed externally between the outside of the assembly and the patient.

* * * * *